United States Patent
Jackman

(10) Patent No.: US 6,852,857 B2
(45) Date of Patent: Feb. 8, 2005

(54) METHOD OF PREPARING SUBSTITUTED 4-AMINO-3-ALKYLTHIO-1,2,4-TRIAZINE-5-ONES

(75) Inventor: Dennis E. Jackman, Prairie Village, KS (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 1 day.

(21) Appl. No.: 10/147,386

(22) Filed: May 16, 2002

(65) Prior Publication Data

US 2003/0216573 A1 Nov. 20, 2003

(51) Int. Cl.[7] ................... C07D 253/07; C07D 253/075
(52) U.S. Cl. ..................................................... 544/182
(58) Field of Search ......................................... 544/182

(56) References Cited

U.S. PATENT DOCUMENTS

| | | | |
|---|---|---|---|
| 3,671,523 A | 6/1972 | Westphal et al. | 260/248 AS |
| 3,905,801 A | 9/1975 | Fawzi | 71/93 |
| 4,035,364 A | * 7/1977 | Dickore et al. | 260/248 |
| 4,131,129 A | 12/1978 | Firestone | 137/596.12 |
| 4,175,188 A | 11/1979 | Klenk et al. | 544/182 |
| 4,309,538 A | 1/1982 | Schmidt et al. | 544/182 |
| 4,346,220 A | 8/1982 | Fawzi | 544/182 |
| 4,402,733 A | * 9/1983 | Pissiotas et al. | 71/93 |
| 5,440,038 A | 8/1995 | Prasad et al. | 544/182 |

* cited by examiner

Primary Examiner—Venkataraman Balasubramanian

(74) Attorney, Agent, or Firm—Richard E. L. Henderson

(57) ABSTRACT

The present invention provides a method of preparing 4-amino-3-alkylthio-1,2,4-triazine-5-ones of the formula (I):

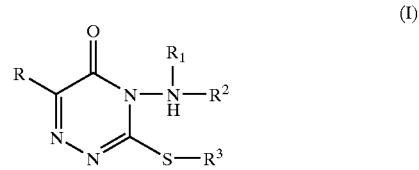

wherein R, $R^1$, $R^2$ and $R^3$ are as defined herein, the method comprising reacting in the presence of a base and under at least one condition selected from the presence of at least one inorganic compound selected from inorganic sulfites and inorganic bisulfites, an inert gas purge, and an alternating inert gas blanket and vacuum, a 4-amino-3-mercapto-1,2,4-triazin-5-one of the formula (II):

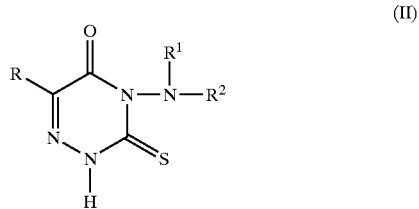

wherein R, $R^1$ and $R^2$ are as defined herein, with an alkylating agent of the formula $R^3$—X, wherein $R^3$ and X are as defined herein and collecting the reaction product.

22 Claims, No Drawings

METHOD OF PREPARING SUBSTITUTED 4-AMINO-3-ALKYLTHIO-1,2,4-TRIAZINE-5-ONES

FIELD OF THE INVENTION

The present invention relates in general to methods of preparing substituted triazinones, and more specifically to methods of preparing substituted 4-amino-3-alkylthio-1,2,4-triazine-5-ones having reduced levels of color.

BACKGROUND OF THE INVENTION

Substituted triazinones, such as 4-amino-3-alkylthio-1,2,4-triazine-5-ones, are useful as herbicides. A number of patents are directed to making triazinones.

U.S. Pat. No. 4,175,188, issued to Klenk et al., teaches methylating 3-mercapto-4-amino-6-t-butyl-1,2,4-triazin-5-one. The method of Klenk involves dissolving 3-mercapto-4-amino-6-t-butyl-1,2,4-triazin-5-one in a mixture of sodium hydroxide solution and methanol followed by treatment of the mixture with methyl iodide.

U.S. Pat. No. 4,309,538 issued to Schmidt et al., teaches alkylating 4-amino-6-t-butyl-3-mercapto-1,2,4-triazin-5(4H)-one. The method of Schmidt treats a mixture of 4-amino-6-t-butyl-3-mercapto-1,2,4-triazin-5(4H)-one, sodium hydroxide solution and water with an alkylating agent, such as methyl iodide or methyl bromide.

One of the problems inherent in those processes is that highly colored impurities, sometimes referred to by those in the art as "color bodies" may be formed during the process. In a commercial setting, color bodies may cause formulation problems and/or result in customer dissatisfaction. Color bodies are not a well understood phenomenon as some workers believe them to be somehow related to increased viscosity, others to unusual crystal structures and still others assert that the color bodies are merely markers for unspecified formulation problems.

To reduce or eliminate formulation problems inherent in the art and/or increase customer satisfaction, therefore, a need exists for a method of preparing a triazinone, such as a substituted 4-amino-3-alkylthio-1,2,4-triazine-5-one, having reduced levels of color.

SUMMARY OF THE INVENTION

Accordingly, the present invention provides a method of preparing a 4-amino-3-alkylthio-1,2,4-trazine-5-one of the formula (I)

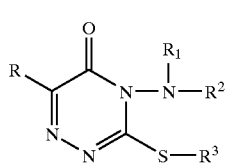

(I)

wherein
R represents $C_3$–$C_8$-alkyl, cycloalkyl having 5–10 ring carbon atoms, unsubstituted or $C_1$–$C_4$-alkyl-, $C_1$–$C_4$-alkoxy-, chloro-, or nitro-substituted phenyl, unsubstituted or chloro-substituted phenylalkyl having 1–4 carbons atoms in the alkyl moiety, chlorophenylalkyl having 1–4 carbons atoms in the alkyl moiety, phenylalkenyl having 2–4 carbon atoms in the alkenyl moiety, phenylalkylmercaptoalkyl having 1–4 carbon atoms in the alkylmercapto moiety and 1–4 carbon atoms in the alkyl moiety, furyl, furfuryl, pyranyl, or pyridylmethyl, $R^1$ and $R^2$ independently represent hydrogen, $C_1$–$C_4$-alkyl, C2–C4-hydroxytrichloro-alkyl, or $C_2$–$C_5$-alkanoyl, and $R^3$ represents $C_1$–$C_{18}$alkyl, the method comprising reacting In the presence of a base and under at least one condition selected from the presence of at least one inorganic compound selected from inorganic sulfites and inorganic bisulfites, an inert gas purge, and an alternating inert gas blanket and vacuum, a 4-amino-3-mercapto-1,2,4-triazin-5-one, of the formula (II)

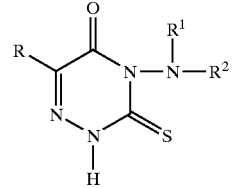

(II)

wherein R, $R^1$ and $R^2$ are as defined above, with an alkylating agent of the formula $R^3$—X, wherein $R^3$ is as defined above and X represents halide, sulfonate, sulfate, phosphate and carbonate, and collecting the reaction product.

The present invention further provides a method of preparing a 4-amino-3-alkylthio-1,2,4-triazine-5-one of the formula (I):

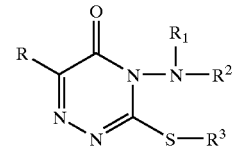

(I)

wherein
R represents cycloalkyl having 5–6 ring carbon atoms, aralkyl having 6–10 ring carbon atoms in the aryl moiety and 1–2 carbon atoms in the alkyl moiety, or aryl group having 6–10 ring carbon atoms, $R^1$ and $R^2$ independently represent hydrogen or $C_1$–$C_4$-alkyl, and $R^3$ represents $C_1$–$C_4$-alkyl, the method comprising reacting in the presence of a base and under at least one condition selected from the presence of at least one inorganic compound selected from inorganic sulfites and inorganic bisulfites, an inert gas purge, and an alternating inert gas blanket and vacuum, a 4-amino-3-mercapto-1,2,4-triazin-5-one of the formula (II):

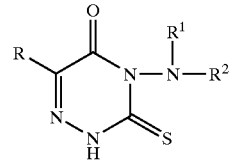

(II)

wherein R, $R^1$ and $R^2$ are as defined above, with an alkylating agent of the formula $R^3$—X, wherein $R^3$ is as defined above and X represents halide, sulfonate, sulfate, phosphate and carbonate, and collecting the reaction product.

The present invention yet further provides a method of decreasing color bodies in a 4-amino-6-alkyl-3-alkylthio-1,2,4-triazin-5(4H)-one of the formula (I):

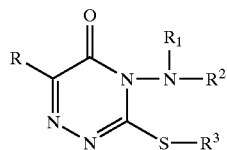

wherein
R represents $C_3$–$C_8$-alkyl, cycloalkyl having 5–10 ring carbon atoms, unsubstituted or $C_1$–$C_4$-alkyl-, $C_1$–$C_4$-alkoxy-, chloro-, or nitro-substituted phenyl, unsubstituted or chloro-substituted phenylalkyl having 1–4 carbons atoms in the alkyl moiety, chlorophenylalkyl having 1–4 carbons atoms in the alkyl moiety, phenylalkenyl having 2–4 carbon atoms in the alkenyl moiety, phenylalkylmercaptoalkyl having 1–4 carbon atoms in the alkylmercapto moiety and 1–4 carbon atoms in the alkyl moiety, furyl, furfuryl, pyranyl, or pyridylmethyl, $R^1$ and $R^2$ independently represent hydrogen, $C_1$–$C_4$-alkyl, $C_2$–$C_4$-hydroxytrichloro-alkyl, or $C_2$–$C_5$-alkanoyl, and $R^3$ represents $C_1$–$C_{18}$-alkyl, the method comprising reacting in the presence of a base and under at least one condition which decreases color bodies in the product selected from the presence of at least one inorganic compound selected from inorganic sulfites and inorganic bisulfites, an inert gas purge, and an alternating inert gas blanket and vacuum, a 4-amino-3-mercapto-1,2,4-triazin-5-one of the formula (II):

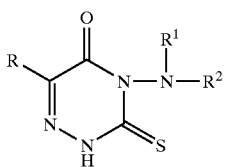

wherein R, $R^1$ and $R^2$ are as defined above, with an alkylating agent of the formula $R^3$—X, wherein $R^3$ is as defined above and X represents halide, sulfonate, sulfate, phosphate and carbonate, and collecting the reaction product.

The present invention still further provides a method of preparing 4-amino-6-t-butyl-3-methylthio-1,2,4-triazin-5(4H)-one comprising reacting in the presence of a base and under a least one condition which reduces the presence of oxygen in a solution, 4-amino-6-t-butyl-3-mercapto-1,2,4-triazin-5(4H)-one with a methylating agent.

The present invention also provides a method of reducing color bodies in 4-amino-6-t-butyl-3-methylthio-1,2,4-triazin-5(4H)-one comprising reacting in the presence of a base and under at least one condition which reduces color bodies selected from the presence of at least one inorganic compound selected from inorganic sulfites and inorganic bisulfites, an inert gas purge, and an alternating inert gas blanket and vacuum, 4-amino-6-t-butyl-3-mercapto-1,2,4-triazin-5(4H)-one with a methyl halide.

The present invention also further provides a method of reducing at least one formulation problem in a reaction mixture comprising 4-amino-6-t-butyl-3-mercapto-1,2,4-triazin-5(4H)-one, a methyl halide and a base, comprising reacting in the presence of a base and under at least one condition which reduces formulation problems selected from the presence of at least one inorganic compound selected from inorganic sulfites and inorganic bisulfites, an inert gas purge, and an alternating inert gas blanket and vacuum, 4-amino-6-t-butyl-3-mercapto-1,2,4-triazin-5(4H)-one with a methyl halide.

These and other advantages and benefits of the present invention will become apparent from the following Detailed Description of the Invention.

DETAILED DESCRIPTION OF THE INVENTION

The present invention will now be described for purposes of illustration and not limitation.

The present invention is directed to the preparation of substituted 4-amino-3-alkylthio-1,2,4-triazine-5-ones, which are low in color, including compounds of the formula (I):

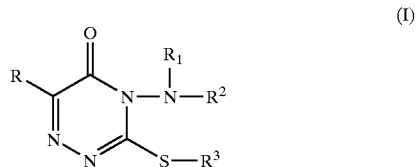

wherein
R represents $C_3$–$C_8$-alkyl, cycloalkyl having 5–10 ring carbon atoms, unsubstituted or $C_1$–$C_4$-alkyl-, $C_1$–$C_4$-alkoxy-, chloro-, or nitro-substituted phenyl, unsubstituted or chloro-substituted phenylalkyl having 1–4 carbons atoms in the alkyl moiety, chlorophenylalkyl having 1–4 carbons atoms in the alkyl moiety, phenylalkenyl having 2–4 carbon atoms in the alkenyl moiety, phenylalkylmercaptoalkyl having 1–4 carbon atoms in the alkylmercapto moiety and 1–4 carbon atoms in the alkyl moiety, furyl, furfuryl, pyranyl, or pyridylmethyl, $R^1$ and $R^2$ independently represent hydrogen, $C_1$–$C_4$-alkyl, $C_2$–$C_4$ -hydroxytrichloro-alkyl, or $C_2$–$C_5$-alkanoyl, and $R^3$ represents $C_1$–$C_{18}$-alkyl.

A group of preferred compounds of the formula (I) are those wherein R represents a cycloalkyl having 5–6 ring carbon atoms, an aralkyl having 6–10 ring carbon atoms in the aryl moiety and 1–2 carbon atoms in the alkyl moiety, or an aryl group having 6–10 ring carbon atoms, $R^1$ and $R^2$ independently represent hydrogen or $C_1$–$C_4$-alkyl, and $R^3$ represents $C_1$–$C_4$-alkyl.

A particularly preferred compound of the formula (I), wherein R represents t-butyl, $R^1$ and $R^2$ both represent hydrogen, and $R^3$ represents methyl is commonly called metribuzin and is available from the assignee of the present invention under the name SENCOR®. The structure of metribuzin is shown below.

Preparation of the substituted 4-amino-3-alkylthio-1,2,4-triazine-5-one of the present invention comprises reacting in the presence of a base, a 4-amino-6-alkyl-3-mercapto-1,2,4-triazin-5(4H)-one of the formula (II):

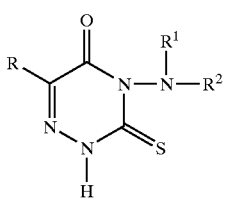

(II)

wherein R, $R^1$ and $R^2$ are as defined above for compounds of the formula (I), with an alkylating agent of the formula $R^3$—X wherein $R^3$ is as defined above for compounds of the formula (I) and X represents halide, sulfonate, sulfate, phosphate or carbonate. The reaction mixture comprising the 4-amino-6-alkyl-3-mercapto-1,2,4-triazin-5(4H)-one, an alkylating agent, and a base may include a solvent, preferably water.

Preferred alkylating agents, $R^3$—X, of the present invention include, but are not limited to, $C_1$–$C_{18}$-alkyl halides, $C_1$–$C_{18}$-alkyl sulfonates and mono- and di-alkylsulfates, $C_1$–$C_{18}$-trialkyl phosphates and $C_1$–$C_{18}$-dialkyl carbonates. More preferably, the alkylating agent is selected from $C_1$–$C_4$ alkyl halides, $C_1$–$C_4$-alkyl sulfonates and mono- and di-alkylsulfates, $C_1$–$C_4$-trialkyl phosphates and $C_1$–$C_4$-dialkyl carbonates. A particularly preferred alkylating agent comprises a methylating agent selected from methyl bromide, ethyl bromide, methyl iodide, ethyl iodide, and dimethyl sulfate.

Preferred bases include, but are not limited to, sodium carbonate and alkali metal hydroxides, such as sodium hydroxide and potassium hydroxide. The base may be in the form of an aqueous composition such as an aqueous composition comprising water and from about 10% to about 50%, preferably about 25%, by weight, sodium hydroxide. Preferably, the amount of the base is sufficient to maintain a basic pH. The pH may be maintained preferably from about 8 to about 12, more preferably from about 10 to about 11.

The reaction of the 4-amino-6-alkyl-3-mercapto-1,2,4-triazin-5(4H)-one with an alkylating agent preferably occurs at a temperature and for a time sufficient for the desired reaction to occur. Preferably, the reaction occurs at a temperature of about 0° C. to about 50° C., more preferably about 20° C. to about 40° C., and for a time of about one hour to about eight hours, more preferably about two hours to about six hours.

Although not wishing to be bound by any theory, the inventor herein speculates that the presence of oxygen during reaction of the 4-amino-6-alkyl-3-mercapto-1,2,4-triazin-5(4H)-one with an alkylating agent results in the formation of color bodies. Therefore, the formation of color bodies is reduced where the reaction with an alkylating agent occurs under at least one of the following conditions, which reduce the amount of oxygen in the mixture:

(a) the presence of at least one inorganic compound selected from inorganic sulfites and inorganic bisulfites, (b) an inert gas purge, (c) an alternating inert gas blanket and vacuum.

Preferred inorganic sulfites and inorganic bisulfites are alkali metal sulfite and alkali metal bisulfites, more preferably sodium sulfite and sodium bisulfite. The inorganic sulfites and/or inorganic bisulfites preferably are present at levels sufficient to reduce the level of color bodies such that little or no color in the resulting product is visible to the eye of an observer.

The ratio of the inorganic sulfite and/or inorganic bisulfite to the 4-amino-6-alkyl-3-mercapto-1,2,4-triazin-5(4H)-one is preferably about 0.2:100 to about 4:100, more preferably about 0.5:100 to about 2:100. The reaction mixture comprising the 4-amino-6-alkyl-3-mercapto-1,2,4-triazin-5 (4H)-one, an alkylating agent, a base and a solvent comprises from about 0.01% to about 0.2% more preferably from about 0.025% to about 0.1%, by weight, inorganic sulfite and/or inorganic bisulfite.

Preferred inert gases include the noble gases and nitrogen, more preferably the inert gas is nitrogen. Where the reaction with an alkylating agent occurs under an inert gas purge, the purge rate preferably is sufficient to reduce the level of color bodies in the resulting product such that little or no color is visible to an observer. Preferred purge rates for a reaction run in a 5000 gallon reactor, for example, are from about 100 to about 10,000, more preferably from about 500 to about 2000 standard cubic feet per hour (scfh).

Where reaction with an alkylating agent occurs under alternating inert gas blanket and vacuum, the system preferably alternates between the inert gas blanket and the vacuum at a rate sufficient to reduce the level of color bodies such that little or no color in the resulting product is visible to the eye. Preferably, the system alternates between the inert gas blanket and the vacuum about every 10 to about 100 minutes, more preferably about every 15 to about 30 minutes. The vacuum is preferably from about 5 to about 200 mm Hg, more preferably from about 20 to about 100 mm Hg. This alternating process may preferably be repeated two to five times.

Although any suitable reaction system, reaction vessel or flask may be used to practice the method of the present invention, the inventor herein prefers that the reaction system utilizing the alternating inert gas blanket and vacuum method be fitted with a Firestone valve, which is described in U.S. Pat. No. 4,131,129.

EXAMPLES

Throughout the following examples and the present specification, unless otherwise specified, parts and percentages are given by weight.

Comparative Example 1

A one liter, four-neck round-bottom flask equipped with a dry ice condenser, mechanical stirrer, pH probe, thermometer and add funnel is charged with 71.4 g of butylthion (4-amino-6-t-butyl-3-mercapto-1,2,4-triazin-5(4H)-one). 512 ml of water is added and 56 g of 25% NaOH solution is added over about one-half hour. 38 g of methyl bromide is added over about one hour and the temperature is maintained at about 25° C. The temperature of the mixture is raised to about 50° C. and maintained for about one hour. The resulting product is cooled, filtered and washed with tap water.

The product has a lilac color as can be seen by reference to Table I, which summarizes the results of this and subsequent examples of the present invention.

Comparative Example 2

The procedure described in Comparative Example 1 is followed, except that MML (metribuzin mother liquor, which is filtrate from a prior metribuzin synthesis) is added to the butylthion instead of water. The procedure also uses 1.43 times the quantity of reactants as Comparative Example 1. The resulting product has a violet color.

Comparative Example 3

The procedure described in Comparative Example 1 was followed, except that 512 ml of a 1:4 mixture of MML and water is added to the butylthion instead of water. The product of this example is gray-pink in color.

Comparative Example 4

Nitrogen Blanket

The procedure described in Comparative Example 3 is followed, except that MML is used instead of the MML/water mixture and the air in the vapor space of the flask is replaced by nitrogen. The resulting product is purple-blue. The inventor speculates that the product is highly colored as a nitrogen blanket may by itself be insufficient to stop color formation because the blanket will not remove oxygen dissolved in the reaction mixture.

As can be appreciated by reference to Table I, all products of the comparative examples have color that is visible to the eye, indicating the presence of color bodies.

Example 5

Nitrogen Blanket/Vacuum 512 ml of MML is placed in a reactor under a nitrogen blanket. 70 g of butylthion is added, followed by 56 g of 25% sodium hydroxide. About halfway through the sodium hydroxide addition, the reactor is alternately subjected to a vacuum and a nitrogen blanket three times. 41.5 g of methyl bromide is added over about one hour at a temperature of about 25° C. The temperature of the mixture is raised to about 50° C. to about 55° C. and maintained for about 2 hours. The resulting metribuzin product is removed by filtration and is washed. The metribuzin appears white, indicating the absence of color bodies.

This example demonstrates that removing dissolved oxygen by vacuum degassing and/or purging the solution with nitrogen reduces color in the resulting product.

Example 6

Nitrogen Purge 500 ml of water is placed in a nitrogen-filled reactor along with 71 g of butylthion. 40 g of 25% sodium hydroxide is added over about five minutes with stirring. The solution is purged of air by adding nitrogen sub-surface for about five minutes at a rate of about 400 ml/min. An additional 16 g of 25% sodium hydroxide is added and 38 g of methyl bromide is added at about 30° C. over about one hour. The solution is heated for about two hours at about 50° C., cooled and a white metribuzin product is obtained after filtering.

Example 7

Sodium Sulfite

A flask is charged with 730 ml of MML and 2 g of sodium sulfite. 102 g of butylthion is added to the flask over about one-half an hour. 80 ml of 25% sodium hydroxide is added to the flask, and the pH is maintained at about 10.5 to about 11.0. The color of this mixture is green.

The temperature is adjusted to about 30° C., and 88.6 g of methyl bromide is added over about one hour. The mixture is heated and the temperature is maintained at about 50° C. to about 55° C. for about two hours. The mixture is cooled to about 15° C. for about 10 minutes, and the metribuzin product is removed by filtration with tap water. The metribuzin appears white-gray in color, indicating a relatively low level of color bodies.

Example 8

Sodium Sulfite

The procedure described in Example 7 is followed, except that the amount of sodium sulfite is reduced from 2 g to 0.7 g. The resulting product is white.

As is apparent by reference to Table I, the methods of the present invention greatly reduce or eliminate color bodies from the product.

TABLE I

| Example No. | Starting Solvent | Nitrogen Treatment | Additive | Product Color |
|---|---|---|---|---|
| C1 | H$_2$O | — | — | lilac |
| C2 | MML | — | — | violet |
| C3 | 1(MML):4(H$_2$O) | — | — | gray-pink |
| C4 | MML | N$_2$ blanket | — | purple-blue |
| 5 | MML | 3x vac/N$_2$ | — | white |
| 6 | H$_2$O | N$_2$ purge | — | white |
| 7 | MML | — | Na$_2$SO$_3$ (2 g) | gray-white |
| 8 | MML | — | Na$_2$SO$_3$ (0.7 g) | white |

MML = metribuzin mother liquor, which is filtrate from a prior metribuzin synthesis.

The foregoing examples of the present invention are offered for the purpose of illustration and not limitation. It will be apparent to those skilled in the art that the embodiments described herein may be modified or revised in various ways without departing from the spirit and scope of the invention. The scope of the present invention is to be measured by the appended claims.

What is claimed is:

1. A method of preparing a 4-amino-3-alkylthio-1,2,4-triazine-5-one of the formula (I):

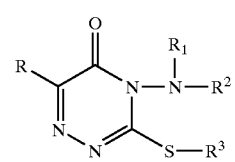

(I)

wherein
R represents C$_{3-C8}$-alkyl, cycloalkyl having 5–10 ring carbon atoms, unsubstituted or C$_1$–C$_4$-alkyl-, C$_1$–C$_4$-alkoxy-, chloro-, or nitro-substituted phenyl, unsubstituted or chloro-substituted phenylalkyl having 1–4 carbons atoms in the alkyl moiety, chlorophenylalkyl having 1–4 carbons atoms in the alkyl moiety, phenylalkenyl having 2–4 carbon atoms in the alkenyl moiety, phenylalkylmercaptoalkyl having 1–4 carbon atoms in the alkylmercapto moiety and 1–4 carbon atoms in the alkyl moiety, furyl, furfuryl, pyranyl, or pyridylmethyl, R$^1$ and R$^2$ independently represent hydrogen, C$_1$–C$_4$-alkyl, C$_2$–C$_4$-hydroxytrichloro-alkyl, or C$_2$–C$_5$-alkanoyl, and R$^3$ represents C$_1$–C$_{18}$-alkyl, comprising:

(a) reacting in the presence of a base a 4-amino-3-mercapto-1,2,4-triazin-5-one of the formula (II):

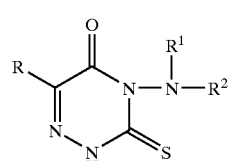

(II)

wherein R, R$^1$ and R$^2$ are as defined above for formula (I), with an alkylating agent of the formula R$^3$—X, wherein
R$^3$ is as defined above for formula (I), and
X represents halide, sulfonate, mono- or dialkyl sulfate, trialkyl phosphate, or dialkyl carbonate;

under one or more reaction conditions consisting of (i) including one or more inorganic sulfites and/or inorganic bisulfites, (ii) carrying out a pre-reaction inert gas purge, (iii) applying an alternating inert gas blanket and vacuum before adding the alkylating agent, or (iv) a combination thereof, and (b) collecting the reaction product.

2. The method of 1, wherein:

R represents t-butyl, $R^1$ and $R^2$ represent hydrogen, and $R^3$ represents methyl.

3. A method of preparing a 4-amino-3-alkylthio-1,2,4-triazine-5-one of the formula (I):

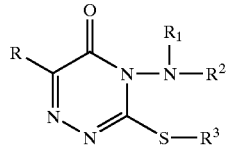

(I)

wherein

R represents cycloalkyl having 5–6 ring carbon atoms, aralkyl having 6–10 ring carbon atoms in the aryl moiety and 1–2 carbon atoms in the alkyl moiety, or aryl group having 6–10 ring carbon atoms, $R^1$ and $R^2$ independently represent hydrogen or $C_1$–$C_4$-alkyl; and $R^3$ represents $C_1$–$C_4$-alkyl, comprising:

(a) reacting in the presence of a base a 4-amino-3-mercapto-1,2,4-triazin-5-one of the formula (II):

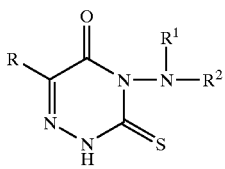

(II)

wherein R, $R^1$ and $R^2$ are as defined above for formula (I), with an alkylating agent of the formula $R^3$—X, wherein:

$R^3$ is as defined above for formula (I), and

X represents halide, sulfonate, mono- or dialkyl sulfate, trialkyl phosphate, or dialkyl carbonate;

under one or more reaction conditions consisting of (i) including one or more inorganic sulfites and/or inorganic bisulfites, (ii) carrying out a pre-reaction inert gas purge, (iii) applying an alternating inert gas blanket and vacuum before adding the alkylating agent, or (iv) a combination thereof, and (b) collecting the reaction product.

4. The method of claim 1, wherein the inorganic sulfite and/or inorganic bisulfite is selected from the group consisting of sodium sulfite and sodium bisulfite.

5. The method of claim 1, wherein the inert gas is selected from the group consisting of the noble gases and nitrogen.

6. The method of claim 1, wherein the alkylating agent of the formula $R^3$—X is selected from the group consisting of $C_1$–$C_{18}$-alkyl halides, $C_1$–$C_{18}$-alkyl sulfonates and mono- and di-alkylsulfates, $C_1$–$C_{18}$-trialkyl phosphates and $C_1$–$C_{18}$-dialkyl carbonates.

7. The method of claim 1, wherein the alkylating agent of the formula $R^3$—X is selected from the group consisting of methyl bromide, ethyl bromide, methyl iodide, ethyl iodide, and dimethyl sulfate.

8. The method of claim 1, wherein the base is selected from the group consisting of sodium carbonate and alkali metal hydroxides.

9. The method of claim 8, wherein the base is sodium hydroxide.

10. A method according to claim 1 of preparing a 4-amino-6-alkyl-3-alkylthio-1,2,4-triazin-5(4H)-one of the formula (I) with concomitant decrease in color bodies:

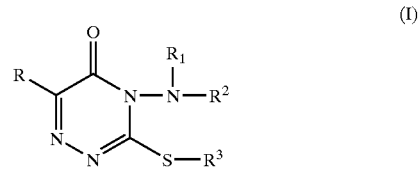

(I)

wherein:

R represents $C_3$–$C_8$-alkyl, cycloalkyl having 5–10 ring carbon atoms, unsubstituted or $C_1$–$C_4$-alkyl-, $C_1$–$C_4$-alkoxy-, chloro-, or nitro-substituted phenyl, unsubstituted or chloro-substituted phenylalkyl having 1–4 carbons atoms in the alkyl moiety, chlorophenylalkyl having 1–4 carbons atoms in the alkyl moiety, phenylalkenyl having 2–4 carbon atoms in the alkenyl moiety, phenylalkylmercaptoalkyl having 1–4 carbon atoms in the alkylmercapto moiety and 1–4 carbon atoms in the alkyl moiety, furyl, furfuryl, pyranyl, or pyridylmethyl, $R^1$ and $R^2$ independently represent hydrogen, $C_1$–$C_4$-alkyl, $C_2$–$C_4$-hydroxytrichloro-alkyl, or $C_2$–$C_5$-alkanoyl, and $R^3$ represents $C_1$–$C_{18}$-alkyl, comprising:

(a) reacting in the presence of a base a 4-amino-3-mercapto-1,2,4-triazin-5-one of the formula (II):

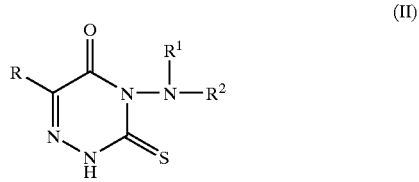

(II)

wherein R, $R^1$ and $R^2$ are as defined above for formula (I), with an alkylating agent of the formula $R^3$—X, wherein:

$R^3$ is as defined above for formula (I), and

X represents halide, sulfonate, mono- or dialkyl sulfate, trialkyl phosphate, or dialkyl carbonate;

under one or more reaction conditions that decrease color bodies consisting of (i) including one or more inorganic sulfites and/or inorganic bisulfites, (ii) carrying out a pre-reaction inert gas purge, (iii) applying an alternating inert gas blanket and vacuum before adding the alkylating agent, or (iv) a combination thereof, and (b) collecting the reaction product.

11. The method of claim 10, wherein the 4-amino-6-alkyl-3-mercapto-1,2,4-triazin-5(4H)-one is a 4-amino-6-$C_1$–$C_6$-alkyl-3-mercapto-1,2,4-triazin-5(4H)-one and the alkylating agent $R^3$—X is selected from the group consisting of $C_1$–$C_4$-alkyl halides, $C_1$–$C_4$-alkyl sulfonates and mono- and di-alkylsulfates, $C_1$–$C_4$-trialkyl phosphates and $C_1$–$C_4$-dialkyl carbonates.

12. The method of claim 10, wherein:

R represents t-butyl, $R^1$ and $R^2$ both represent hydrogen, and $R^3$ represents methyl.

13. The method of claim 10, wherein the inorganic sulfite and/or inorganic bisulfite is selected from the group consisting of sodium sulfite and sodium bisulfite.

14. The method of claim 10, wherein the inert gas is selected from the group consisting of the noble gases and nitrogen.

15. A method of preparing 4-amino-6-t-butyl-3-methylthio-1,2,4-triazin-5(4H)-one comprising:

(a) reacting in the presence of a base 4-amino-6-t-butyl-3-mercapto-1,2,4-triazin-5(4H)-one with a methylating agent under a condition that reduces the presence of oxygen in a solution by (i) including one or more inorganic sulfites and/or inorganic bisulfites, (ii) carrying out a pre-reaction inert gas purge, (iii) applying an alternating inert gas blanket and vacuum before adding the alkylating agent, or (iv) a combination thereof, and (b) collecting the reaction product.

16. The method of claim 15, wherein the methylating agent is methyl bromide, methyl iodide or dimethyl sulfate.

17. The method of claim 15, wherein the base is an aqueous alkali metal hydroxide solution and the methylating agent is a methyl halide.

18. The method of claim 17, wherein the base is an aqueous sodium hydroxide solution and the methylating agent is methyl bromide.

19. A method according to claim 1 of preparing 4-amino-6-t-butyl-3-methylthio-1,2,4-triazin-5(4H)-one with concomitant reduction of color bodies comprising:

(a) reacting in the presence of a base 4-amino-6-t-butyl-3-mercapto-1,2,4-triazin-5(4H)-one with a methyl halide, under one or more reaction conditions that reduce color bodies consisting of (i) including one or more inorganic sulfites and/or inorganic bisulfites, (ii) carrying out a pre-reaction inert gas purge, (iii) applying an alternating inert gas blanket and vacuum before adding the alkylating agent, or (iv) a combination thereof, and (b) collecting the reaction product.

20. The method of claim 19, wherein the inorganic sulfite and/or inorganic bisulfite is selected from the group consisting of sodium sulfite and sodium bisulfite.

21. The method of claim 19, wherein the inert gas is selected from the group consisting of the noble gases and nitrogen.

22. The method of claim 21, wherein the inert gas is nitrogen.

* * * * *